United States Patent [19]

Müller et al.

[11] Patent Number: 5,616,728
[45] Date of Patent: Apr. 1, 1997

[54] ORGANIC CHARGE TRANSFER COMPLEX

[75] Inventors: Harald Müller, München, Germany; Yoshinobu Ueba, Osaka, Japan

[73] Assignee: Sumitomo Electric Industries, Ltd., Osaka, Japan

[21] Appl. No.: 540,154

[22] Filed: Oct. 6, 1995

Related U.S. Application Data

[63] Continuation of Ser. No. 195,028, Feb. 14, 1994, abandoned.

[30] Foreign Application Priority Data

Feb. 12, 1993 [JP] Japan .................................... 5-024490

[51] Int. Cl.[6] .......................... C07D 339/06; C07C 50/06
[52] U.S. Cl. ............................................. 549/11; 552/303
[58] Field of Search ................................ 549/11; 552/303

[56] References Cited

PUBLICATIONS

Synthetic Metals, vol. 42, No. 1–2, 1991, Amsterdam NL, pp. 1963–1970, R.P. Shibaeva et al, "New cation–radical salts based on BEDT–TTF Analogs with Polyhalide Anions" *pp. 1963–1965*.
Synthetic Metals, vol. 2, No. 3, 1991, Amsterdam NL, pp. 2409–2413, H. Nakano et al "Synthesis of multi–chalcogen TTF–derivatives and electrical conductivities of their radical–ion salts" *pp. 2409–2411; table 2*.
Chemistry Letters No. 11, 1990, Tokyo JP, pp. 2129–2132, H. Nakano et al "Synthesis of 4,5–ethylene dithio–4'5'–(2–oxatrimethylenedithio)–tetrathiafulvalene (EOTT) and electrical conductivities of their ion–radical salts" *p. 2130; table 1*.
Journal of Molecular Electronics, vol. 5, No. 1, 1989, Chichester GB, pp. 33–36, V. Khodorkovsy et al, "Electron––donating ability of tetrathiafulvalene derivatives invedtigated by cyclic voltammetry" *pp. 33–34; table 1*.

Chemical Abstracts, vol. 111, No. 13, 25 Sep. 1989, Columbus, Ohio, US; abstract No. 115150b.
R. Medne et al "Synthesis and crystal structure of bis(oxapropylenedithio) tetrathiafulvalene hexyfluorophosphate", p. 661; *abstract* & Izv. Akad. Nauk SSSR, Ser. Khim. No. 1, 1989, pp. 174–176.
Bulletin of the Chemical Society of Japan, vol. 66, No. 6, Jun. 1993, Tokyo JP, pp. 1773–1777.
H. Muller et al "Synthesis and properties of bis(oxybid(Methylenethio)tetrathiafulvalene ad its sulfur analog: pi–donor for organic metals" *pp. 1773–1775*.

Primary Examiner—José G. Dees
Assistant Examiner—Mary C. Cebulak
Attorney, Agent, or Firm—Sughrue, Mion, Zinn, Macpeak & Seas

[57] ABSTRACT

An organic charge transfer complex comprising an electron donor and an electron acceptor, the electron donor is at least one of bis(oxapropylenedithio)tetrathiafulvalene represented by formula (1):

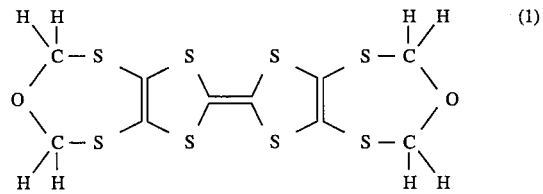

and bis(thiapropylenedithio)tetrathiafulvalene represented by formula (2):

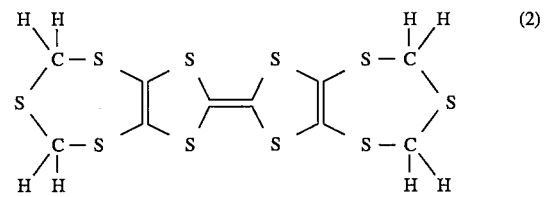

6 Claims, No Drawings

ORGANIC CHARGE TRANSFER COMPLEX

This is a continuation of application No. 08/195,028 filed Feb. 14, 1994, now abandoned.

FIELD OF THE INVENTION

The present invention relates to an organic charge transfer complex, and more particularly to an organic charge transfer complex which is expected to be applied to organic electrically conductive materials, organic superconductive materials, organic magnetic substances, organic electrochromic materials, and organic electroluminescent materials.

BACKGROUND OF THE INVENTION

Compounds which are expected to be applied to the above-described fields, such as organic electrically conductive materials, organic superconductive materials, organic magnetic substances, organic electrochromic materials, and organic electroluminescent materials, include an organic charge transfer complex comprising an electron donors (donor molecule) and an electron acceptor ( acceptor molecule or anion ), as described in "TTF-TCNQ Complexes and Related Materials", (written by Gunji Saito and Kunihiko Yamaji) in *The Elements of Chemistry*, No. 42, (Chemistry of Conductive Low Dimensional Materials) (1983) edited by Chemical Society of Japan, published by the publishing Gakkai Shuppan Center, Japan.

Examples of the conventional donor molecules include compounds having a fulvalene skeleton such as tetrathiafulvalene (TTF), tetramethyltetraselenafulvalene (TMTSF), and bisethylenedithiatetrathiafulvalene (BEDT-TTF). Examples of the conventional acceptor molecules include tetracyanoquinodimethane (TCNQ). Examples of the conventional anions include hexafluorophosphate anion ($PF_6^-$), perchlorate anion ($ClO_4^-$) and triiodide anion ($I_3^-$).

Typical examples of the conventional organic charge transfer complexes include electrically conductive complexes such as TTF-TCNQ ($\sigma_{RT}$=500 s/cm) and TMTSF-TCNQ ($\sigma_{RT}$=800 s/cm) and superconductive complexes such as $(TMTSF)_2ClO_4$ (critical temperature Tc=1.4K), β-$(BEDT-TTF)_2I_3$ (Tc=8K), κ-$(BEDT-TTF)_2Cu(NCS)_2$ (Tc=10.4K) and κ-$(BEDT-TTF)_2Cu(N(CN)_2)Cl$ (Tc=13K).

However, any of the conductive complexes that are put to practical use at present has a problem in that anisotropy in electrical conductance is high. Further, among the superconductive complexes that are put to practical use at present, the compound having the highest critical temperature is the above-described κ-$(BEDT-TTF)_2Cu(N(CN)_2)Cl$ having Tc=13K, and any compound having a critical temperature higher than that described above cannot be obtained at present.

Accordingly, it is demanded to develop novel complexes having characteristics which conventional complexes do not possess, such as conductive complexes having low anisotropy in electrical conductivity, superconductive complexes having a higher critical temperature, and complexes having excellent characteristics as semiconductors.

SUMMARY OF THE INVENTION

Accordingly, an object of the present invention is to provide an organic charge transfer complex which is free from the problems associated with the prior art.

Another object of the present invention is to provide conductive complexes having low anisotropy in electrical conductivity, superconductive complexes having a higher critical temperature, and complexes having excellent characteristics as semiconductors.

Other objects and effects of the present invention will be apparent from the following description.

The present inventors have made an analysis of electric conduction mechanisms of organic charge transfer complexes comprising donor molecules having a fulvalene skeleton which are put to practical use at present. As a result, they have found that anisotropy in electrical conductivity is caused by the crystal structures of the organic charge transfer complexes.

It is known that general organic charge transfer complexes have a separate laminate type crystal structure, in which a donor molecule and an acceptor molecule or an anion stand in separate lines to form separate columns, respectively. The donor molecule having a fulvalene skeleton is arranged so that the planar fulvalene skeleton is put parallel within the column.

Charge migrates from the donor molecule to the acceptor molecule or the anion, and a carrier generated on the column of the donor molecule migrates through the crystal along the molecular orbital spreading in the direction of the column. As a result, electrical conductivity is developed. The donor molecule having a fulvalene skeleton had such a tendency that its molecular orbital spreads one-dimensionally or two-dimensionally, and therefore anisotropy in electrical conductivity is produced.

In the case of BEDT-TTF represented by formula (3), such molecular orbital as described above is apt to spread two-dimensionally. Therefore, when BEDT-TTF is used in combination with an anion, a laminar two-dimensional structure composed of a donor layer and an anion layer is formed, the interaction of the donor layers is reduced by the effect of the anion layer adjacent thereto, and anisotropy in electrical conductance is thus further increased.

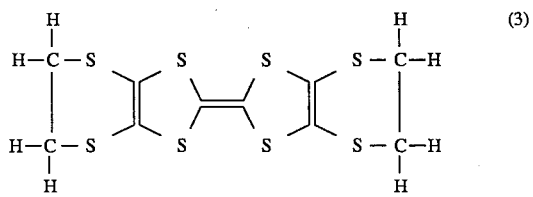

(3)

The present inventors have made studies on the molecular orbital of the BEDT-TTF molecule, and have found that when an oxygen atom or a sulfur atom is introduced into the ethylene group positioned near the anion, the spreading of the molecular orbital in the direction perpendicular to the in-plane direction of the donor layer is increased, and the molecular orbital has three-dimensional spreading, and at the same time, the interaction of the donor layers is increased and as a result, the anisotropy in electrical conductivity can be canceled. Further, the present inventors have found that when anisotropy in electrical conductivity is canceled, the electrical conductivity of the organic charge transfer complexes can be improved, and there is a possibility that superconductive complexes having a critical temperature higher than that of κ-$(BEDT-TTF)_2Cu(N(CN)_2)Cl$ (Tc=13K) can be obtained and complexes having excellent characteristics as semiconductors can be obtained.

The present invention provides an organic charge transfer complex comprising an electron donor and an electron acceptor, the electron donor is at least one of bis(oxapropylenedithio)tetrathiafulvalene (hereinafter referred to as BOPDT-TTF) represented by formula (1):

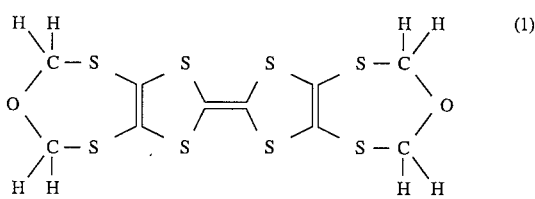

and bis(thiapropylenedithio)tetrathiafulvalene (hereinafter referred to as BTPDT-TTF) represented by formula (2):

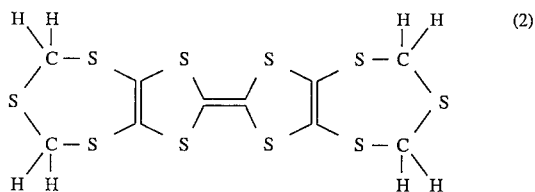

DETAILED DESCRIPTION OF THE INVENTION

BOPDT-TTF of formula (1) and BTPDT-TTF of formula (2) can be synthesized by various synthesis methods. In a preferred embodiment, a precursor represented by formula (4):

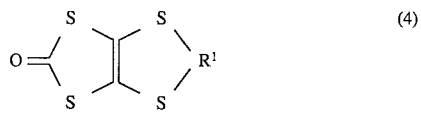

(wherein $R^1$ represents $-CH_2-O-CH_2-$ or $-CH_2-S-CH_2-$) is heated in the presence of a trialkyl phosphite with stirring to couple two molecules, thereby synthesizing the compound. This method is preferred from the standpoint of production efficiency and safety.

The precursor of formula (4) can be synthesized by various methods. In a preferred embodiment, 1,3,4,6-tetrathiapentalene-2,5-dione is reacted in an alcohol solution containing a methoxide of an alkaline metal under an inert atmosphere at a temperature of 30° C. or lower, to selectively open one of its rings, thereby producing 1,3-dithiol-2-one-4,5-dithiolate dianion, which is then reacted with a compound containing a divalent organic group corresponding to the group $R^1$ in formula (4). This method is preferred from the standpoint of production efficiency and safety.

The electron acceptor which can be used in combination with the above BOPDT-TTF and/or BTPDT-TTF is not particularly limited and includes conventional acceptor molecules and anions. Examples of the acceptor molecules include tetracyanoquinodimethanes such as tetracyanoquinodimethane (TCNQ) and derivatives thereof; tetracyanoethylenes such as tetracyanoethylene (TCNE) and hexacyano-1,3-butadiene; fluorenones such as fluorenone and trinitrofluorenone (TNF); and p-benzoquinones such as p-fluoranyl and dichlorodicyano-p-benzoquinone. Examples of the anions include halogen anions such as $Br^-$, $I^-$, $Cl^-$, $I_3^-$ and $Br_2^-$; planar type anions such as $NO_3^-$; tetrahedral type anions such as $BF_4^-$, $ClO_4^-$ and $ReO_4^-$; octahedral type anions such as $PF_6^-$, $AsF_6^-$, $SbF_6^-$ and $TaF_6^-$; and metal halogenoid anions such as $Cu(NCS)_2^-$, $Cu(N(CN)_2)X^-$ (wherein X is Br, Cl, etc.), $Cu(N(CN)_2)CN^-$, $Cd(NCS)_2^-$, $Zn(NCS)_2^-$, $Hg(NCS)_2^-$ and $KHg(NCS)_4^-$. Among the above, TCNQ and an iodine anion are preferably used as the electron acceptor.

The organic charge transfer complex of the present invention can be prepared from the above BOPDT-TTF and/or BTPDT-TTF and the above-described electron acceptors by conventional methods such as solution methods, diffusion methods, and methods for preparing a single crystal by electrolytic crystal growth. Further, a method for preparing a complex by heating an electron donor and an electron acceptor in a solution, as described in H. Müller, *Synthetic Metals*, vol. 39, pp. 261–267 (1990), and a method for preparing fine powder of a complex crystal by ultrasonic treatment.

The organic charge transfer complex of the present invention alone or together with an appropriate binder can be processed into various forms such as powder-compressed sheets, wires, films, membranes, etc. and can be applied to organic electrical conductive materials, organic superconductive materials, organic electrochromic materials, organic electroluminescent materials, etc.

The present invention is now illustrated in greater detail by reference to the following examples which, however, are not to be construed as limiting the invention in any way.

EXAMPLE 1

50 mg (0.12 mmol) of BOPDT-TTF of formula (1) and 24.5 mg (0.12 mmol) of TCNQ as the electron acceptor were weighed and placed in a reaction vessel. The reaction vessel was purged with argon, and 20 ml of chlorobenzene was introduced into the reaction vessel with a syringe. Subsequently, the reaction vessel was heated to a reflux temperature, maintained at that temperature for 10 minutes, and then cooled to room temperature to terminate the reaction. A black precipitate was recovered by filtration, washed with methylene chloride and then pentane and dried under reduced pressure to obtain 58.6 mg (yield: 76%) of the reaction product in the form of powder.

The elemental analysis of the reaction product was made, and the following results were obtained.
Elemental analysis for the reaction product:
 Found: C, 42.71%; H, 1.95%; N, 8.84%
Elemental analysis for (BOPDT-TTF)TCNQ complex:
 Calculated: C, 42.56%; H, 1.95%; N, 9.02%

The found values were well-consistent with the calculated values. Accordingly, it was confirmed that the reaction product was a complex of BOPDT-TTF/TCNQ=1/1.

The above-obtained (BOPDT-TTF)TCNQ complex was subjected to infrared spectrophotometric analysis. Absorption peaks were found at 2,205 $cm^{-1}$, 1,560 $cm^{-1}$, 1,522 $cm^{-1}$, 1,302 $cm^{-1}$, 1,046 $cm^{-1}$, 913 $cm^{-1}$, 803 $cm^{-1}$, 675 $cm^{-1}$, and 468 $cm^{-1}$. Strong electron absorption vibration was found in the region of from 4,000 to 1,500 $cm^{-1}$. It was confirmed that a peak ascribed to the stretching vibration of the CN group of TCNQ was shifted from 2224 $cm^{-1}$ to 2204 $cm^{-1}$, which showed that a partial charge transfer from the donor molecule (BOPDT-TTF) to the acceptor molecule (TCNQ) occurred.

An ESR analysis of the (BOPDT-TTF)TCNQ complex showed a q value of 2.004 and a line width of 7 G, which was close to the q value of free electrons of 2.0029. The spin density was $4 \times 10^{23}$ spins/mol.

The (BOPDT-TTF)TCNQ complex powder was compression molded into a sheet. The resistance of the sheet was measured by means of a four terminal method. The resistance was 110 $m\Omega cm^{-1}$ (electrical conductivity: 10 S/cm).

For the purpose of comparison, bis(propylenedithio)tetrathiafulvalene (hereinafter referred to as BPDT-TTF) wherein $-CH_2-$ group was introduced in place of the oxygen atom in formula (1) was used to prepare (BPDT-TTF)TCNQ complex in the same manner as above. The sheet prepared from the (BPDT-TTF)TCNQ complex had a resistance of 16 Ωcm (electrical conductivity: 0.06 S/cm). It is clear from these results that the (BOPDT-TTF)TCNQ complex according to the present invention has an improved electrical conductance.

EXAMPLE 2

A chlorobenzene solution containing 71 mg (0.56 mmol) of iodine dissolved therein was added to a solution of 50 mg (0.11 mmol) of BTPDT-TTF of formula (2) in 100 ml of chlorobenzene in an argon atmosphere. The mixture was stirred overnight at room temperature. A black precipitate was collected from the reaction mixture by filtration and washed with carbon tetrachloride to remove residual iodine. The precipitate was dried under reduced pressure to obtain 65 mg (yield: 85%) of the reaction product in the form of powder.

The elemental analysis of the reaction product was made, and the following results were obtained.
Elemental analysis for the reaction product:
  Found: C, 18.78%, H, 1.00%
Elemental analysis for (BTPDT-TTF)$_2$I$_3$ complex:
  Calculated: C, 18.66%; H, 1.25%

The found values were well-consistent with the calculated values. Accordingly, it was confirmed that the reaction product was a complex of BTPDT-TTF/I$^-$=⅔.

The above-obtained (BTPDT-TTF)$_2$I$_3$ complex was subjected to infrared spectrophotometric analysis. Absorption peaks were found at 1,423 cm$^{-1}$, 1,364 cm$^{-1}$, 1,218 cm$^{-1}$, 1,164 cm$^{-1}$, 1,124 cm$^{-1}$, 877 cm$^{-1}$, 852 cm$^{-1}$, 810 cm$^{-1}$, 769 cm$^{-1}$, 720 cm$^{-1}$, 517 cm$^{-1}$, and 478 cm$^{-1}$.

An ESR analysis of the (BTPDT-TTF)$_2$I$_3$ showed a q value of 1.9958, a line width of 180 G, and a spin density of 1.49×10$^{23}$ spins/mol.

The electrical conductance of the (BTPDT-TTF)$_2$I$_3$ complex was 2.4×10$^{-7}$ S/cm on the level of semiconductor.

As described above, the organic charge transfer complex of the present invention has low anisotropy and high conductivity in comparison with conventional tetrathiafulvalene complexes, and it can be expected that the organic charge transfer complex of the present invention can be applied to superconductive materials having a high critical temperature, conductive materials having a wide range of electrical conductivity ranging from semiconductors to metallic materials, magnetic substances, electrochromic materials, and electroluminescent materials. Accordingly, it can be highly expected that the organic charge transfer complex of the present invention can be applied to various wiring materials, wires, printed circuits, sensors, elements, shielding materials, reflective materials, photoconductive materials, and magnetic materials.

While the present invention has been described in detail and with reference to specific embodiments thereof, it is apparent to one skilled in the art that various changes and modifications can be made therein without departing from the spirit and the scope of the present invention.

What is claimed is:

1. An organic charge transfer complex comprising an electron donor and an electron acceptor, said electron donor is represented by formula (1):

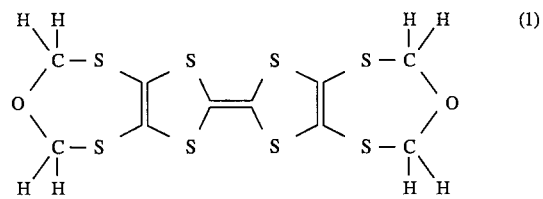

said electron donor being produced by a process comprising:
  subjecting 1,3,4,6-tetrathiapentalene-2,5-dione to a ring opening reaction to produce 1,3-dithiol-2-one-4,5-dithiolate dianion;
  reacting said 1,3-dithiol-2-one-4,5-dithiolate dianion with a compound containing a divalent organic group selected from the consisting of —CH$_2$—O—CH$_2$— or —CH$_2$—S—CH$_2$—, to produce a precursor represented by formula (4):

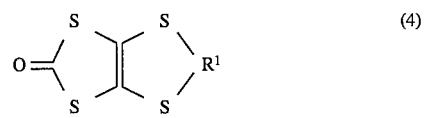

wherein R$^1$ represents —CH$_2$—O—CH$_2$— or —CH$_2$—S—CH$_2$—; and
  coupling two molecules of said precursor to produce said electron donor;
  and said electron acceptor is tetracyanoquinodimethane.

2. The organic charge transfer complex as claimed in claim 1, wherein said ring opening reaction of 1,3,4,6-tetrathiapentalene-2,5-dione is effected in an alcohol solution containing a methoxide of an alkaline metal under an inert atmosphere.

3. The organic charge transfer complex as claimed in claim 2, wherein said ring opening reaction of 1,3,4,6-tetrathiapentalene-2,5-dione is effected at a temperature of 30° C. or lower, to selectively open one of its rings.

4. An organic charge transfer complex comprising an electron donor and an electron acceptor, said electron donor is represented by formula (1):

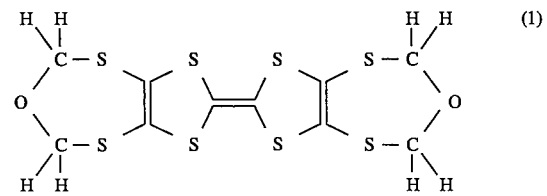

said electron donor being produced by a process comprising:
  subjecting 1,3,4,6-tetrathiapentalene-2,5-dione to a ring opening reaction to produce 1,3-dithiol-2-one-4,5-dithiolate dianion;
  reacting said 1,3-dithiol-2-one-4,5-dithiolate dianion with a compound containing a divalent organic group selected from the consisting of —CH$_2$—O—CH$_2$— or —CH$_2$—S—CH$_2$—, to produce a precursor represented by formula (4):

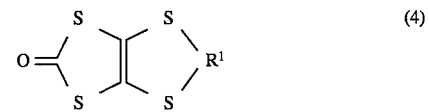

wherein R$^1$ represents —CH$_2$—O—CH$_2$— or —CH$_2$—S—CH$_2$—, and coupling two molecules of said precursor to produce said electron donor;

and said electron acceptor is $I_3^-$.

5. The organic charge transfer complex as claimed in claim 4, wherein said ring opening reaction of 1,3,4,6-tetrathiapentalene-2,5-dione is effected in an alcohol solution containing a methoxide of an alkaline metal under an inert atmosphere.

6. The organic charge transfer complex as claimed in claim 5, wherein said ring opening reaction of 1,3,4,6-tetrathiapentalene-2,5-dione is effected at a temperature of 30° C. or lower, to selectively open one of its rings.

* * * * *